United States Patent
Miyoshi

(12) 
(10) Patent No.: US 6,339,446 B1
(45) Date of Patent: *Jan. 15, 2002

(54) ENDOSCOPIC IMAGE DISPLAY SYSTEM AND METHOD FOR THE SAME THAT DISPLAYS ON HI-VISION MONITOR

(75) Inventor: Yoshitaka Miyoshi, Hachioji (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/430,173

(22) Filed: Apr. 27, 1995

Related U.S. Application Data

(63) Continuation of application No. 07/819,189, filed on Jan. 10, 1992, now abandoned.

(30) Foreign Application Priority Data

Jan. 14, 1991 (JP) .............................. 3-002678
Oct. 24, 1991 (JP) .............................. 3-277877

(51) Int. Cl.$^7$ .......................... A61B 1/04; A61B 1/045; H04N 7/18
(52) U.S. Cl. .......................... 348/65; 348/74; 600/109; 600/118
(58) Field of Search .............................. 348/65, 68, 69, 348/71, 73, 74, 77; 345/145, 146; 358/98; 128/6; 364/413.13; 600/118, 109

(56) References Cited

U.S. PATENT DOCUMENTS

| | | | | |
|---|---|---|---|---|
| 4,772,882 A | * | 9/1988 | Mical | 340/723 |
| 4,877,016 A | * | 10/1989 | Kantor et al. | 348/65 |
| 4,920,413 A | * | 4/1990 | Nakamura et al. | 358/98 |
| 4,935,810 A | | 6/1990 | Nonami et al. | 358/98 |
| 5,031,036 A | * | 7/1991 | Kikuchi et al. | 358/98 |
| 5,045,935 A | * | 9/1991 | Kikuchi | 358/98 |
| 5,111,306 A | * | 5/1992 | Kanno et al. | 358/98 |
| 5,187,579 A | * | 2/1993 | Hiyama | 358/98 |

FOREIGN PATENT DOCUMENTS

GB  2157036  * 10/1985

* cited by examiner

*Primary Examiner*—Howard Britton
(74) *Attorney, Agent, or Firm*—Armstrong, Westerman, Hattori, McLeland & Naughton, LLP.

(57) ABSTRACT

An endoscopic image display system has a recording apparatus for recording an endoscopic image signal, a retrieval apparatus connected with the recording apparatus so as to retrieve an image recorded in the recording apparatus, the retrieval apparatus generating a retrieval-character image signal for an operation to effect such a retrieval, a hi-vision monitor for displaying an endoscopic image from the recording apparatus which has been retrieved by the retrieval apparatus; and an image display control apparatus for outputting to the hi-vision monitor a retrieval-character image signal from the retrieval apparatus, and for controlling the outputting of a plurality of image signals in such a manner that a retrieval-character image is displayed together with the endoscopic image by the monitor on the same screen.

5 Claims, 8 Drawing Sheets

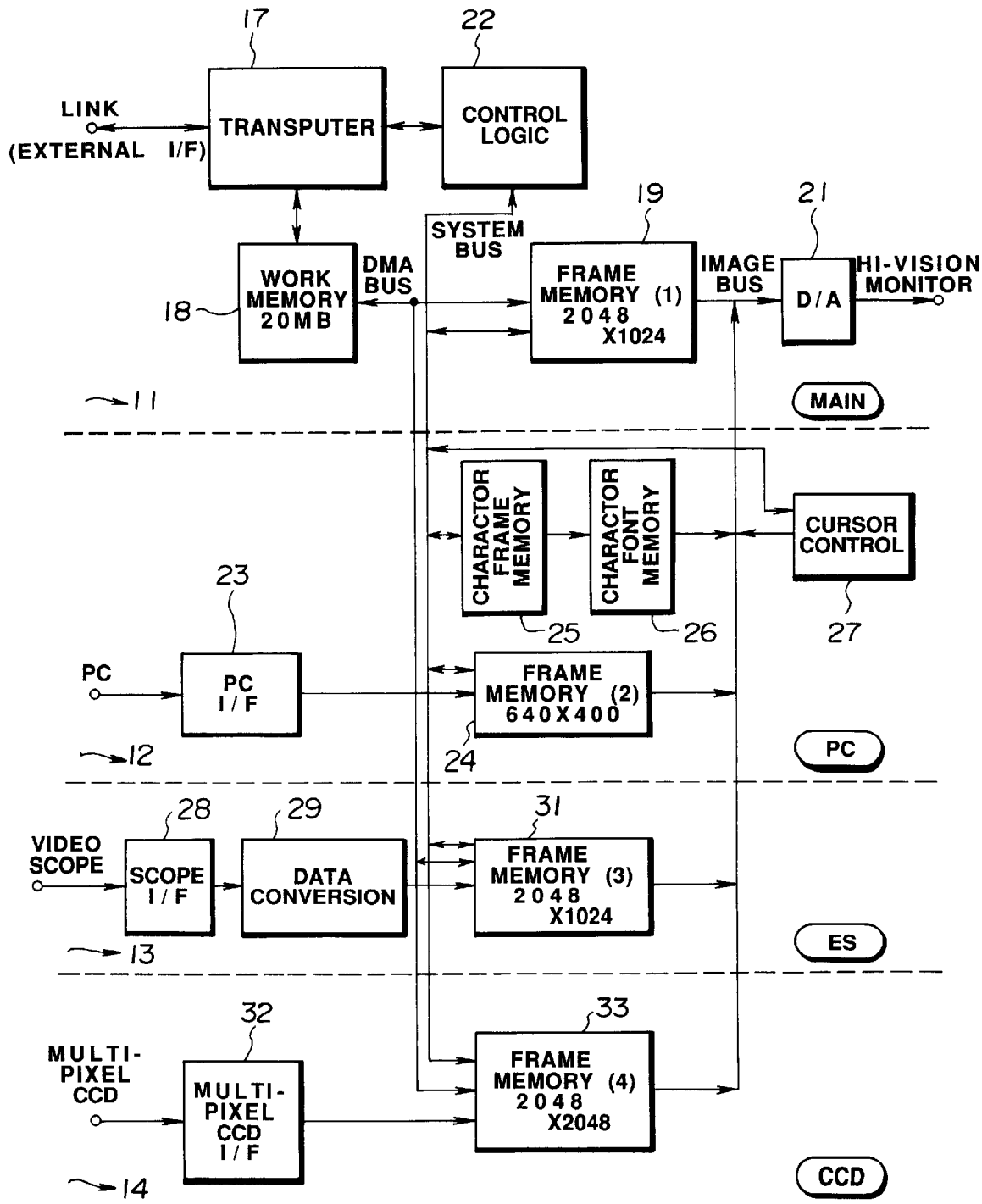

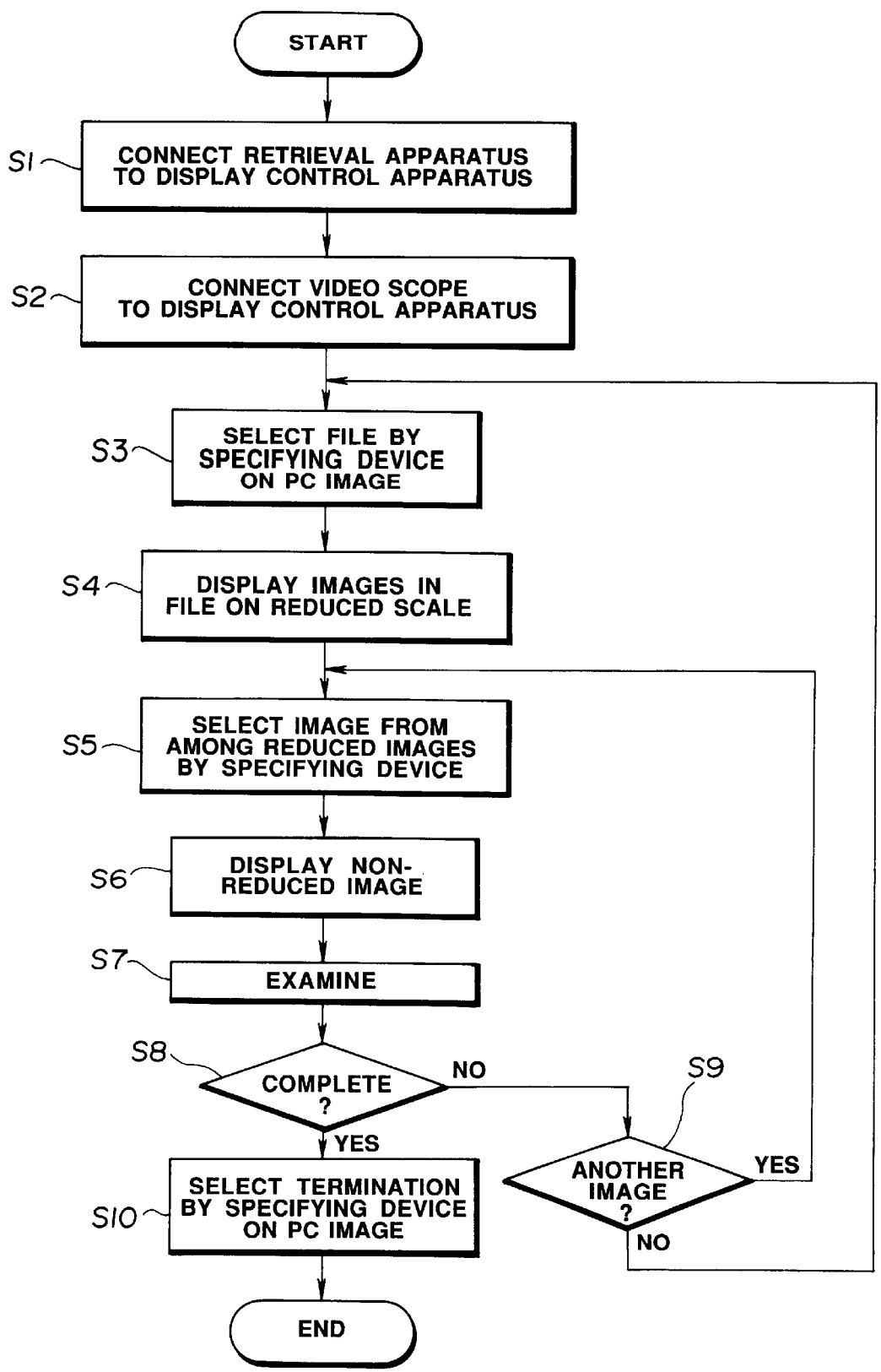

ENDOSCOPIC IMAGE DISPLAY SYSTEM AND METHOD FOR THE SAME THAT DISPLAYS ON HI-VISION MONITOR

This application is a continuation of application Ser. No. 07/819,189 filed Jan. 10, 1992, now abandoned.

BACKGROUND OF THE INVENTION

1. Field of the Invention

The present invention relates to an endoscopic image display system for displaying an endoscopic image or the like already recorded in a recording apparatus onto a high definition monitor (hereinafter referred to as "hi-vision monitor").

2. Description of the Related Art Statement

An endoscope enables, as is well known, the observation of the inside of an organism, etc., that cannot be directly observed by eye, and is widely used in medical and other fields for the purposes of observation and diagnosis. In recent years the use of, electronic endoscopes have spread, which allows an image of the object of observation to be converted into an electrical signal by an imaging means such as a CCD so that the image can be observed with a monitor.

Such electronic endoscopes have an advantage in that images can be easily recorded and reproduced. With an endoscope of this type, therefore, it is possible to perform a diagnosing by referring to images such as those which have previously been recorded. In this way, a more accurate diagnosis can be given.

To this end, a system has been hitherto known, in which an endoscopic image is retrieved from a recording apparatus by a retrieval apparatus (consisting of a personal computer or the like), and then displayed for diagnosing, etc. During a retrieval operation employing this system, the user performs a predetermined retrieval procedure by moving a cursor on a screen for retrieval operations, which screen is on a monitor for the personal computer and which is now being watched by the user. Then, the user recognizes the image resulting from the retrieval on another monitor for displaying an endoscopic image.

However, with the above-described conventional display system, in order to effect a retrieval, the user has to perform a retrieval procedure while he watches the screen of the monitor connected with the personal computer, and, in order to observe the thus retrieved image, the user has to watch the screen of the other monitor for displaying an endoscopic image. Thus, the display system has poor operability.

A possible means to overcome this drawback is a display system capable of displaying a plurality of images. When such a system is to be used in a diagnosis utilizing an endoscopic image, the system is desired to have the function of displaying a plurality of images with a minimum reduction in the image resolution.

However, since display has hitherto been effected on a monitor having a limited level of resolution, problems arise in that the resolution of the endoscopic images lowers, and that the number of images that can be displayed is inevitably limited. Further, with the conventional display system, it has been difficult to simultaneously display on a single screen both a display image of a computer (serving as a retrieval apparatus) and an endoscopic image.

SUMMARY OF THE INVENTION

An object of the present invention is to provide an endoscopic image display system that is capable of displaying a plurality of images with a minimum reduction in the image resolution, and is thus capable of allowing an image for an operation for effecting a retrieval from a retrieval means to be simultaneously displayed on a monitor displaying an endoscopic image. In consequence, the system enables all of: a retrieval operation; the recognition of a retrieved endoscopic image; and a diagnosing through an endoscopic image to be performed while a single screen is being watched.

Another object of the present invention is to provide an endoscopic image display system that is capable of allowing both an observation image obtained by an endoscope and a recorded endoscopic image comprising a still image to be displayed on the same screen, the system also allowing an image for a retrieval-effecting operation to be simultaneously displayed on that same screen. The system thus enables a target recorded image to be retrieved while endoscopic observation is being performed so that comparison of an endoscopic image and diagnosis through the endoscopic image are easily performed.

A further object of the present invention is to provide an endoscopic image display system that is capable of displaying a plurality of images on the same screen without reducing the resolution, and also capable of displaying an image having high-resolution information on that same screen without reducing the image quality.

According to the present invention, an endoscopic image display system comprises: a recording apparatus for recording an endoscopic image signal; retrieval means connected with the recording apparatus so as to retrieve an image recorded in the recording apparatus, the retrieval means generating a retrieval-character image signal for an operation to effect such a retrieval; a hi-vision monitor for displaying an endoscopic image from the recording apparatus which has been retrieved by the retrieval means; and image display control means for outputting to the hi-vision monitor a retrieval-character image signal from the retrieval means, and for controlling the outputting of a plurality of image signals in such a manner that a retrieval-character image is displayed together with the endoscopic image by the monitor on the same screen.

Other features and advantages of the present invention will become fully apparent from the following description.

BRIEF DESCRIPTION OF THE DRAWINGS

FIGS. 1 through 5 illustrate a first embodiment of the present invention, in which, FIG. 1 is a block diagram showing the construction of the whole of an endoscopic image display system;

FIG. 2 is a block diagram showing the construction of an image display control apparatus;

FIG. 3 is an explanatory view showing display regions for various types of images;

FIG. 4 is a flowchart showing a flow during an endoscopic examination; and

FIG. 5 is an explanatory view showing an example of the display of various images on a hi-vision monitor.

FIGS. 6 through 9 illustrate a second embodiment of the present invention, in which FIG. 6 is a block diagram showing the construction of the whole of an endoscopic image display system;

FIG. 7 is an explanatory view showing display regions for various types of images;

FIG. 8 is a flowchart showing a flow during an endoscopic examination; and

FIG. 9 is an explanatory view showing an example of the display of various images on a hi-vision monitor.

DETAILED DESCRIPTION OF THE PREFERRED EMBODIMENTS

Figure 1:
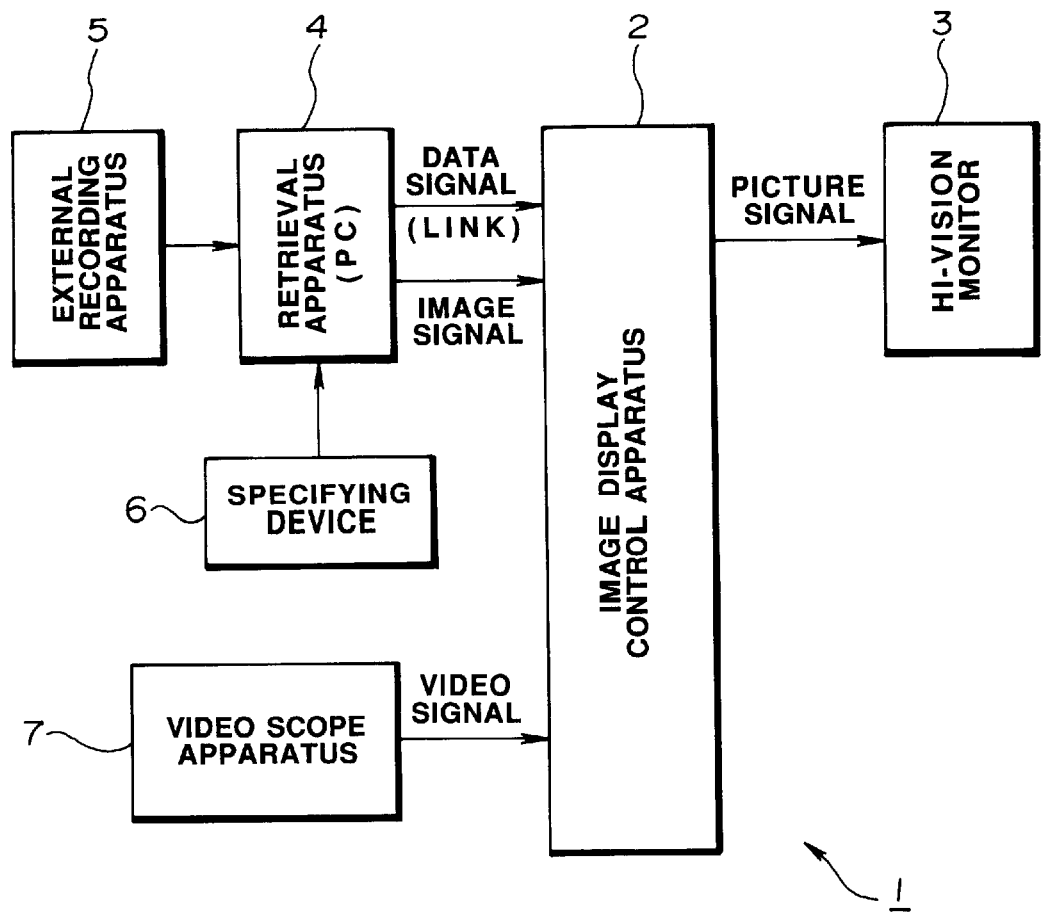
Figure 3:
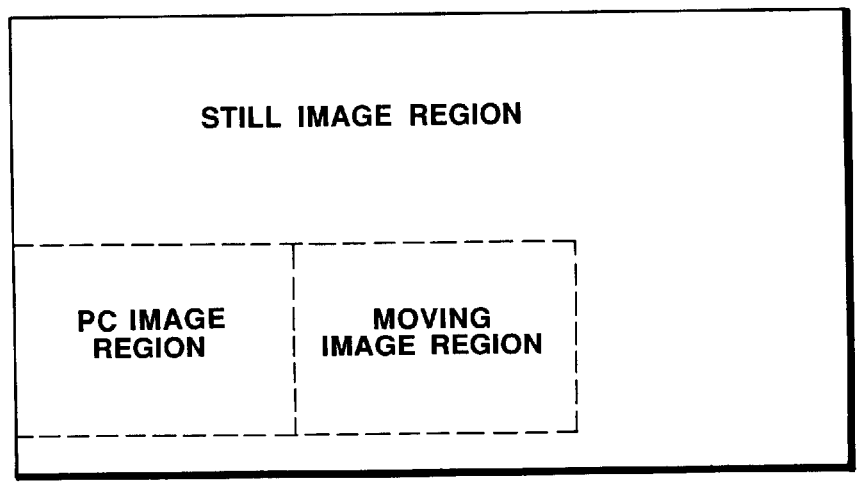

FIGS. 1 through 5 illustrate a first embodiment of the present invention. As shown in FIG. 1, an endoscopic image display system 1 comprises an image display control apparatus 2 (serving as image display control means) configured in accordance with various functions to facilitate extension, and composed of a plurality of (for instance, four) basic boards in which gate arrays consisting of logic cell arrays (LCAs) are adopted, a hi-vision (high resolution) monitor 3 for displaying a hi-vision picture signal output from the image display control apparatus 2, a retrieval apparatus 4 (serving as retrieval means) which consists of a personal computer 4 (abbreviated to "PC") and which is adapted to output an image-data signal and an image signal (each indicating a type of image, as will be described later), an external recording apparatus 5 serving as an image file apparatus for recording images which may be retrieved by the retrieval apparatus 4, a specifying device 6 for outputting a specifying signal to the retrieval apparatus 4, and a video scope apparatus 7 for outputting a video signal indicative of an endoscopic image to the image display control apparatus 2.

As shown in FIG. 2, the image display control apparatus 2 is configured in accordance with a plurality of functions so as to facilitate extension. Specifically, the apparatus 2 comprises a main (MAIN) board 11 serving as main control means which mainly performs control over the boards as well as processing for the purpose of displaying filed images, a PC board 12 serving as retrieval image control means mainly capable of inputting a personal computer image (PC image) from the retrieval apparatus 4 to a frame memory in a real time manner, an ES board 13 serving as endoscopic image control means mainly capable of inputting an endoscopic image from the video scope apparatus 7 to a frame memory in a real time manner, and a CCD board 14 serving as high-resolution image control means mainly capable of inputting an image from a multi-pixel CCD to a frame memory in a real time manner.

The MAIN board 11 comprises a transputer 17 consisting of, e.g., a 32-bit RISC chip computer, a work memory 18 having a large capacity of, e.g., 20 Mbyte, a frame memory (1) 19 for still images that has, e.g., 2048×1024 dots, a D/A converter 21 for processing an image output of the frame memory 19, and a control logic circuit 22 which is programmable and which serves as a system controller.

The MAIN board 11 also performs, in addition to the above-described control over the various boards and the processing for filed image display, control over the composition processing of image signals from the other boards, and control over direct memory access (DMA) transfer between memories.

An external interface (I/F) renders the transputer 17 capable of being connected to the external recording apparatus 5 serving as the image recording means with either only the I/F therebetween or the I/F and the retrieval apparatus 4 therebetween (FIG. 1 shows the latter case). For instance, image data consisting of reduced image data and non-reduced image data, which has been read from the external recording apparatus 5 with the intervention of the retrieval apparatus 4 (such as a PC), passes through a data signal line to be input to the MAIN board 11, in which items of the image data are, via the transputer 17, the control logic circuit 22 and a system bus, sequentially written into predetermined locations of the still image frame memory (1) 19. The image data, thus transferred to the still image frame memory (1) 19, is converted into a part of an analog picture signal by the D/A converter 21 and, thereafter, output to the hi-vision monitor 3 via an image bus, whereupon the part of the picture signal is displayed on the screen of the hi-vision monitor 3 in, for example, the manner shown in FIG. 5.

In this case, the image data within an image file, which has been retrieved by the retrieval apparatus 4 and which corresponds to a reduced image-scale, is transferred to the still image frame memory (1) 19 so that a plurality of reduced still images SG are simultaneously displayed on an upper section of the screen of the hi-vision monitor 3. When one image is selected from among the plurality of reduced still images SG, the selected still image is displayed as a non-reduced still image HG on a right lower section of the screen, thus the screen simultaneously displaying the non-reduced still image HG and the reduced still images SG.

The retrieved image data may be subjected to reducing and other necessary processing by the transputer 17. Alternatively, image data already brought into correspondence with a reduced image-scale by the retrieval apparatus 4 may be input to the transputer 17.

It is also possible to record image data in the large-capacity work memory 18 into the external recording apparatus 5. The transputer 17 cooperates with the control logic circuit 22 to control the various boards which are connected with the transputer 17 via the control logic circuit 22 and the system bus.

The PC board 12 comprises a PC I/F 23 allowing the PC board 12 to be connected with the PC 4 (serving as the retrieval apparatus) in conformity therewith, a PC image frame memory (2) 24 having, e.g., 640×400 dots, a character frame memory 25, a character font memory 26, and a cursor control circuit 27. The PC board 12 inputs a PC image in the form of a digital data having one bit for each of red (R), green (G) and blue (B) to the frame memory (2) 24 in a real time manner, and outputs the PC image to the D/A converter 21 via the image bus. After the PC image has been converted by the D/A converter 21 into a part of an analog picture signal, the part of the picture signal is displayed, as an image, at an arbitrarily chosen position of the screen on the hi-vision monitor 3 in a real time manner.

Figure 5:
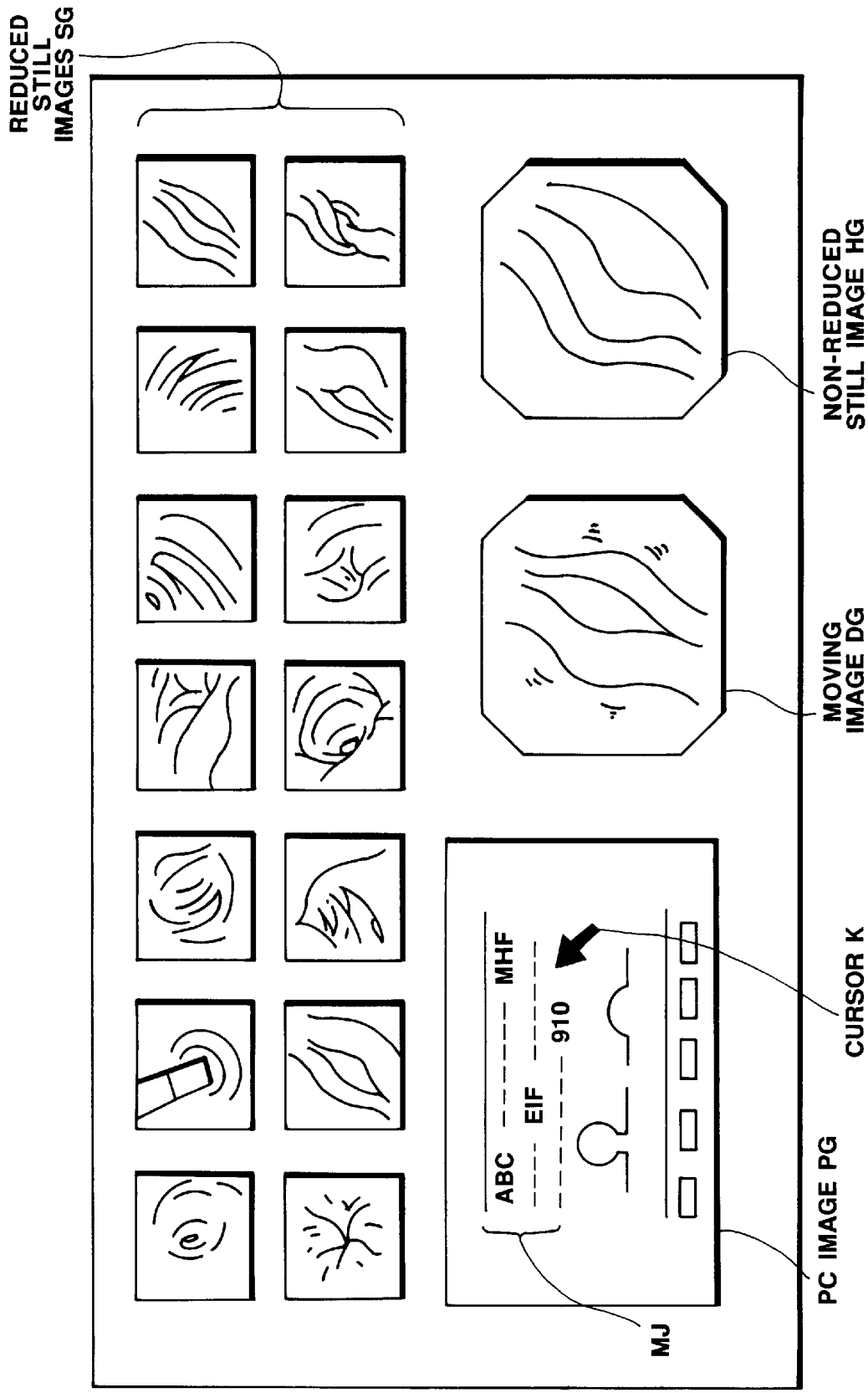

For instance, as shown in FIG. 5, a PC image PG is displayed on the screen on the lower left side of the reduced still images SG, that is, at a position on one side of the non-reduced still image HG. In this case, it is possible to effect simultaneous display of character information MJ prepared by the retrieval apparatus 4, and also to effect, by the operation of the two memories, i.e., the character font memory 26 and the character frame memory 25, superimpose display of the character information in any desired color(s) on the screen of the hi-vision monitor 3. Further, the cursor control circuit 27, connected with the control logic circuit 22 via the system bus, enables a cursor K and a cross-bar cursor, each within 32×32 dots and of an arbitrary shape, to be superimpose-displayed in any desired color (s) on the display screen similarly to the above-described character display. The control logic circuit 22 renders the cursor K movable to any desired position within the whole display screen.

The ES board 13 comprises a scope I/F 28 allowing the ES board 13 to be connected with the video scope apparatus 7 in conformity therewith (the video scope apparatus 7 being connected with a video scope accommodating a solid-state imaging device, such as a CCD, at the forward end of an elongated inserting section), an image data conversion circuit 29 for converting image data input through the scope I/F 28, and a video image frame memory (3) 31 for inputting the image data resulting from the conversion by the image data conversion circuit 29, the frame memory (3) 31 having, e.g., 2048×1024 dots. The ES board 13 subjects a video image, input as a R-G-B analog signal, to real-time A/D conversion, inputs the converted image data to the frame memory (3) 31, and outputs the image data to the D/A converter 21 via the image bus. The D/A converter 21 converts the output into a part of an analog picture signal so that, as shown in FIG. 5, a video moving image DG is displayed at an arbitrarily chosen position on the screen of the hi-vision monitor 3, for example, at a position between the non-reduced still image HG and the PC image PG.

When image data is to be input to the frame memory (3) 31, the image data conversion circuit 29 enables the image data to be subjected certain data conversion which allows the display of image data subjected to data conversion such as black-white inversion, enlargement and/or reduction. An enlargement of image data is possible to an enlargement scale of about to 1:4, and the enlarged image data is input to the frame memory (3) 31.

The CCD board 14 comprises a multi-pixel CCD I/F 32 allowing the CCD board 14 to be connected with a multi-pixel imaging device (having a multi-pixel CCD) in conformity therewith, and an image frame memory (4) 33. The CCD board 14 inputs a high-resolution image signal (input as an analog or digital signal) to the frame memory (4) 33 in a real time manner, and outputs the signal to the D/A converter 21 via the image bus. The D/A converter 21 converts the output signal to a part of an analog picture signal, which part of the signal will be displayed at an arbitrarily chosen position of the screen of the hi-vision monitor 3. An example of an usable multi-pixel imaging device is a multi-pixel CCD camera having a CCD provided with a multi-pixel imaging surface and capable of obtaining a high-resolution image.

In the endoscopic image display system 1 having the above-described construction, reduced and non-reduced images are read from the external recording apparatus 5 (consisting of a magneto-optic disk apparatus or the like) by the retrieval apparatus 4. The thus read images are passed through the data signal line (link) to be input to the MAIN board 11 of the image display control apparatus 2, in which the images are, via the transputer 17, the control logic circuit 22 and the system bus, sequentially written into predetermined locations of the frame memory (1) 19.

A PC image is output from a digital R-G-B image output of the retrieval apparatus 4, and input to the PC board 12 of the image display control apparatus 2 in such a manner that the PC image is, via the PC I/F 23, written into a predetermined location of the frame memory (2) 24. The image data is updated all the time (that is, input in a real time manner).

An analog R-G-B video output from the video scope apparatus 7 which corresponds to a moving image is input to the ES board 13 of the image display control apparatus 2, in which the video output is subjected to analog-to-digital conversion by the scope I/F 28, subjected to necessary data processing (such as data interpolation in the case of enlargement or data omission in the case of reduction) by the data conversion circuit 29, and written into a predetermined location of the frame memory (3) 31. The image data is updated all the time (that is, inputted in a real time manner). Whenever necessary, the updating can be interrupted, and a still image can be displayed on the screen of the hi-vision monitor 3. Alternatively, an image freezing may be effected by the video scope apparatus 7, and a video signal indicative of the resultant still image may be inputted to the ES board 13.

The various types of image data thus written into the three memories, i.e., the frame memory (1) 19, the frame memory (2) 24 and the frame memory (3) 31, are sequentially read to the image bus at different timings in correspondence with a plurality of display regions (such as those shown in FIG. 3), and then displayed, via the D/A converter 21, onto the respective positions of the screen of the hi-vision monitor 3.

The reading of the items of the image data is switched for example, in the following manner: At a display timing for displaying in a still image region (among the regions shown in FIG. 3), image data is read from the still image frame memory (1) 19. At a display timing for displaying in a PC image region, image data is read from the PC image frame memory (2) 24. Similarly, at a timing for displaying in a moving image region, image data is read from the video image frame memory (3) 31. The read image data is outputted to the D/A converter 21.

In addition, a command from the retrieval apparatus 4 causes a cursor to be overlaid (preferentially displayed) at an arbitrary position of the screen. The D/A converter 21 performs digital-to-analog conversion of the data on the read images and the cursor so as to convert the data into a picture signal in conformity with certain hi-vision standards. The signal is output to the hi-vision monitor 3, which displays various images in, for example, the manner shown in FIG. 5.

The work memory 18, the frame memory (1) 19, the frame memory (3) 31 and the frame memory (4) 33 are connected to each other by a DMA bus so that image data can be transferred between these memories. For instance, image data, such as image data from the video scope apparatus which has been written in the frame memory (31) 31 of the ES board 13 and image data from the multi-pixel CCD camera apparatus which has been written in the frame memory (4) 33 of the CCD board 14, can be transferred via the DMA bus to the work memory 18 so that the transferred image data may be recorded in the external recording apparatus 5.

Further, the frame memory (1) 19, the frame memory (2) 24, the frame memory (3) 31 and the frame memory (4) 33 are connected to the system bus, and thus connected to the control logic circuit 22, which controls the writing and reading of image data with respect to these memories. Still further, the character frame memory 25 is connected to the system bus while the character font memory 26 is connected to the image bus so that image data serving as character information is sent via the D/A converter 21 to the hi-vision monitor 3.

The image display control apparatus 2 enables the above-described plurality of types of images to be displayed on the hi-vision monitor 3 at a high resolution of, for example, 1920 dots in the horizontal direction and 1035 dots in the vertical direction. The image display control apparatus 2 also has the function of displaying, for example, at a resolution of 1280 dots in the horizontal direction and 1024 dots in the vertical direction in 16,800,000 colors in a non-interlace manner.

A target image may be selected from among a plurality of reduced still images SG by either specifying a particular item of retrieval data among the retrieval data items within a PC image PG or directly specifying one of a plurality of reduced still images SG. Further, a target image may be specified by, without displaying a cursor K by the cursor control circuit 27 on the monitor 3, assigning symbols to retrieval candidate reduced images SG or items of retrieval data within a PC image PG, and by directly inputting one of the symbols through the specifying device 6, so that the specified image is displayed as a non-reduced image HG. In this case, the cursor control circuit 27 is not necessary.

FIG. 4 shows the details of a typical operation performed in examination employing the endoscopic image display system 1. After the examination has started, the retrieval apparatus 4 is connected to the image display control apparatus 2 (Step S1) so that a PC image PG will always be displayed at a display position on the screen of the hi-vision monitor 3 which corresponds to the PC image region shown in FIG. 3. In Step S2, the video scope apparatus 7 is connected to the image display control apparatus 2 so that a video scope image (moving image DG) will always be displayed at another display position on the screen corresponding to the moving image region shown in FIG. 3.

Subsequently, the retrieval function of the PC 4 is started. Specifically, when, in Step S3, a file recorded in the external recording apparatus 5 is selected by means of the specifying device 6 on the PC image, the images within the file are displayed, in Step S4, as a plurality of reduced images SG on the screen of the hi-vision monitor 3.

Then, in Step S5, the desired image is selected from among the plurality of reduced images SG. For example, a past image of the affected portion whose present image is now being obtained by the video scope apparatus 7, is selected. In Step S6, the selected image is displayed as a non-reduced image HG on the screen of the hi-vision monitor 3 at a position next to the video scope image.

Accordingly, when the operator compares the non-reduced image HG and the video scope image with each other, he can, in Step S7, examine the affected portion in order to judge whether the portion has, for instance, improved or worsened.

Thereafter, if it is determined, in Step S8, that the examination is not yet to be completed, Step S9 is executed to determine whether or not another image in the same file is to be selected. If it is determined, in Step S9, that no further image is to be selected, Step S3 et seq. are executed. On the other hand, if it is determined, in Step S8, that the examination is to be completed, Step S10 is effected, in which termination is selected by means of the specifying device 6 on the PC image, thereby terminating the flow for the examination.

In this embodiment, some of the images already stored in the recording apparatus 5 are displayed as retrieval candidate images on a reduced scale, a target image is selected from among the plurality of reduced images SG, and the selected image is displayed as a non-reduced image HG. Alternatively, a target image may be retrieved by using a retrieval-character image within the PC image PG so that the thus retrieved image is displayed as a non-reduced image HG.

The endoscopic image display system 1 according to this embodiment has the following advantageous features:

(a) The configuration in which a plurality of boards are provided in accordance with their respective functions enables various functions to be realized through combinations.

(b) When the principal circuits are composed of programmable logics, it is possible to cope with other display methods.

(c) The bus configuration includes, in addition to the bus for system control and the bus for image outputting, the DMA bus for high-speed transfer between memories. This enables image data to be transferred at high-speed.

(d) The basic boards consists of the four boards, i.e., the MAIN board 11, the PC board 12, the ES board 13 and the CCD board 14.

According to this embodiment, it is possible to: display images in an image file in the external recording apparatus 5; display a PC image PG including character information in a real time manner; display moving image DG obtained by the video scope apparatus 7; and display characters and a moving image from the multi-pixel CCD. It is also possible to arbitrarily compose these images, and to display the result of the composition on the hi-vision monitor 3.

Furthermore, the hi-vision monitor has a high resolution, and a great aspect ratio. Therefore, the hi-vision monitor allows a plurality of images to be displayed on the same screen, and the display of the plurality of images involves only a little omission of information on the individual images.

These features make it possible to compare a moving image DG resulting from the visualization of the affected portion by the video scope apparatus 7 with a non-reduced image HG from an image file without involving a reduction in the resolution. This means that the system has many advantages. Among them, there are an advantage in that changes of the affected portion with the passage of time can be easily found, and an advantage in that a plurality of reduced still images SG can be simultaneously displayed, thereby eliminating a disadvantage of the conventional system (employing a monitor which is not a hi-vision monitor) in that display has been possible only within a narrow display region in a selective manner. The above-described advantages render a plurality of items of image information available for the operator, thereby realizing an environment with which the operator can easily make a diagnosis. Another advantage is that an operation to effect selective display, which has been necessary with the narrow display region of the conventional system, can be greatly relaxed.

Although FIG. 5 illustrates the case where only the three frame memories (1) 19, (2) 24 and (3) 31 are used, an image obtained by the multi-pixel CCD may also be displayed on the hi-vision monitor 3. Further, characters can be displayed by writing character codes into arbitrary positions of the character frame memory 25 so that the character font memory 26 causes characters converted into corresponding image data (symbols, etc.) are displayed (overlaid) at positions on the screen which correspond to the addresses of the character frame memory 25.

The manners in which an image file may be selected include not only the manner in which an image file is selected by specifying a particular item of character information on the PC image PG but also the manner in which selection is made by moving a cursor K to the position of a target image among the reduced still images SG and then specifying the image by, for instance, clicking on the screen.

FIGS. 6 through 9 illustrate a second embodiment of the present invention.

The second embodiment is an example in which a multi-pixel CCD camera apparatus for obtaining microscopic images is used as an external apparatus connected with a CCD board 14 such as that described above.

Figure 6:
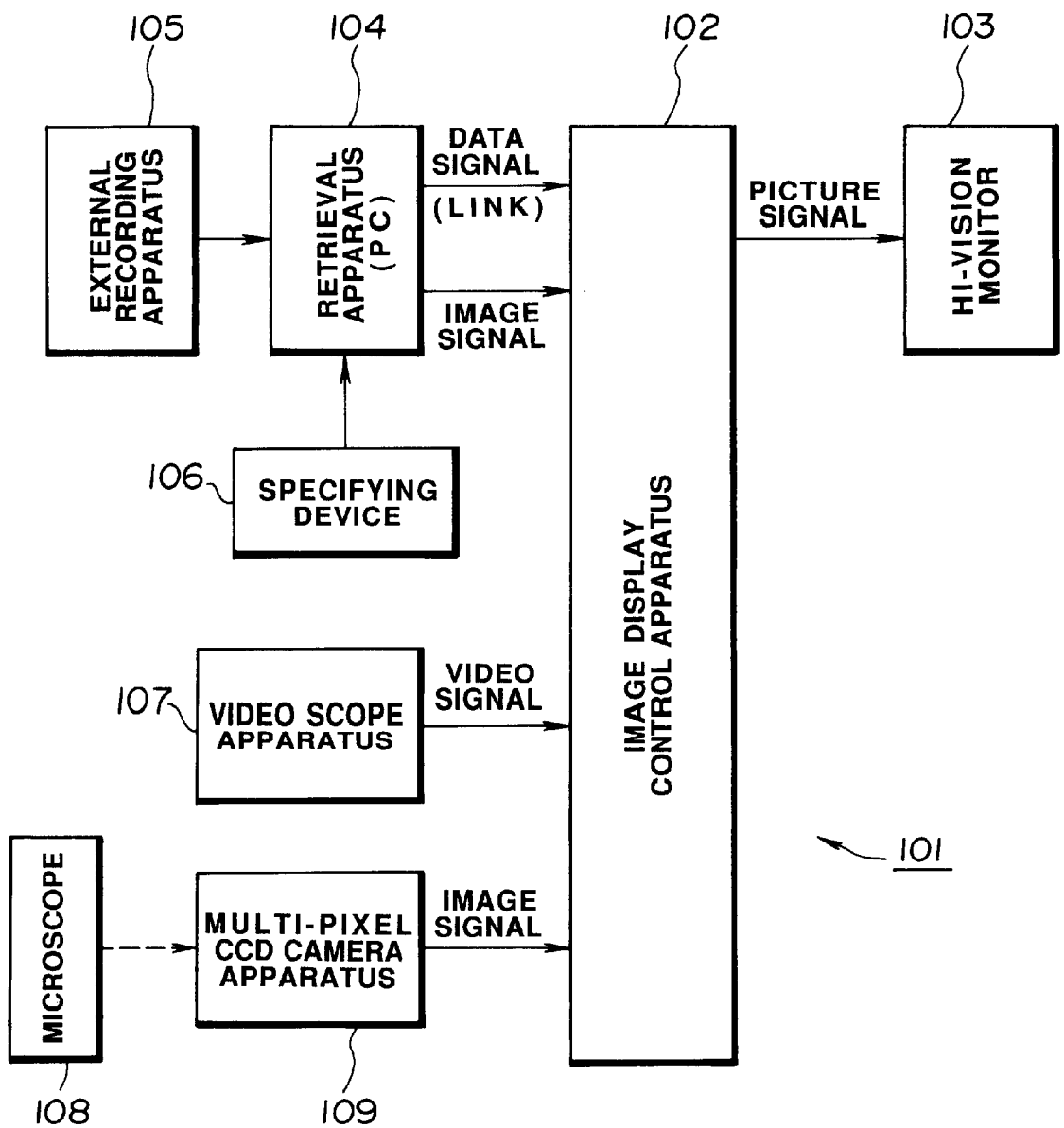

As shown in FIG. 6, an endoscopic image display system 101 comprises an image display control apparatus 102, a hi-vision monitor 103 for displaying a picture signal output from the image display control apparatus 102, a retrieval apparatus 104 which consists of a personal computer (PC) or the like and which is adapted to output an image-data signal and an image signal, an external recording apparatus 105 for recording images which may be retrieved by the retrieval apparatus 104, a specifying device 106 for outputting a specifying signal to the retrieval apparatus 104, a video scope apparatus 107 for outputting a video signal indicative of an endoscopic image to the image display control apparatus 102, a multi-pixel CCD camera apparatus 109 for outputting an image signal indicative of a pathological image of a lesion portion to the image display control apparatus 102, and a microscope 108 for outputting an optical image to the multi-pixel CCD camera apparatus 109. Thus, in the second embodiment, the microscope 108 and the multi-pixel CCD camera apparatus 109 for obtaining a microscopic image from the microscope 108 are added to the construction of the first embodiment shown in FIG. 1.

The image display control apparatus 102 comprises, similarly to the corresponding apparatus of the first embodiment shown in FIG. 2, four boards, that is, a MAIN board 11, a PC board 12, an ES board 13 and a CCD board 14. As shown in FIG. 2, the CCD board 14 comprises a multi-pixel CCD I/F 22 allowing the CCD board 14 to be connected with the multi-pixel CCD camera apparatus 109 (for obtaining an optical image from the microscope 108) in conformity therewith, and an image frame memory (4) 33. An image signal input from the multi-pixel CCD camera apparatus 109 is written into a frame memory (4) 33 in a real time manner, and input to a D/A converter 21 via an image bus. The D/A converter 21 converts the input signal to a part of a picture signal, which signal will be displayed by the hi-vision monitor 103. An example of an usable multi-pixel CCD camera apparatus is a camera apparatus of this kind which is adapted for a hi-vision system.

Figure 7:
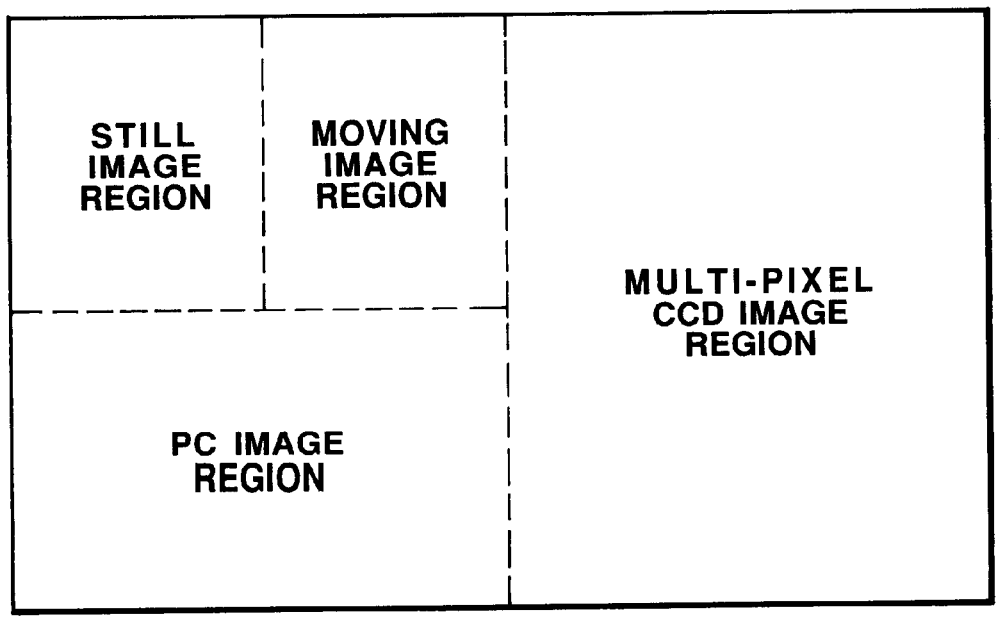

In the second embodiment, display regions for various types of images are set in a manner such as that shown in FIG. 7. A plurality of images are displayed on the screen of the hi-vision monitor 103 in, for example, the manner shown in FIG. 9. Specifically, an image from the MAIN board 11 is displayed at a position for a file image FG at an upper left section of the screen. An image from the PC board 12 is displayed at a position for a PC image PG at a lower left section of the screen. An image from the ES board 13 is displayed at a position for a moving image DG which is on the right side of the file image FG position. An image from the CCD board 14 is displayed at a position for a microscopic image KG on the right side of the screen. Further, a cursor K having an arbitrary shape and controlled by a cursor control circuit 27 as well as character information prepared by a character frame memory 25 and a character font memory 26 are displayed (superimposed) on the screen in any desired color(s).

In the endoscopic image display apparatus 101, a file image FG is read from the external recording apparatus 105 by the retrieval apparatus 104, and passed through a data signal line to be input to the MAIN board 11 of the image display control apparatus 102, in which the file image FG is written, via a transputer 17, a control logic circuit 22 and a system bus, into a predetermined location of a frame memory (1) 19. A PC image PG is output from an image output of the PC 104 serving as the retrieval apparatus, and input to the PC board 12 of the image display control apparatus 102, in which the PC image PG is written, via a PC I/F 23, into a predetermined location of a frame memory (2) 24 in a real time manner.

A moving image DK is output from a video output of the video scope apparatus 107, and input to the ES board 13 of the image display control apparatus 102, in which the moving image DG is subjected to A/D conversion by a scope I/F 28 and to necessary data processing (such as data interpolation in the case of enlargement or data omission in the case of reduction) by a data conversion circuit 29 and, thereafter, the resultant image is written into a predetermined location of a frame memory (3) 31 in a real time manner. With respect to a microscopic image KG, a high-resolution image signal output from the multi-pixel CCD camera apparatus 109 is input to the CCD board 14 within the image display control apparatus 102, in which the signal is A/D converted by the multi-pixel CCD I/F 32, and written into a predetermined location of the frame memory (4) 33 in a real time manner.

Figure 9:
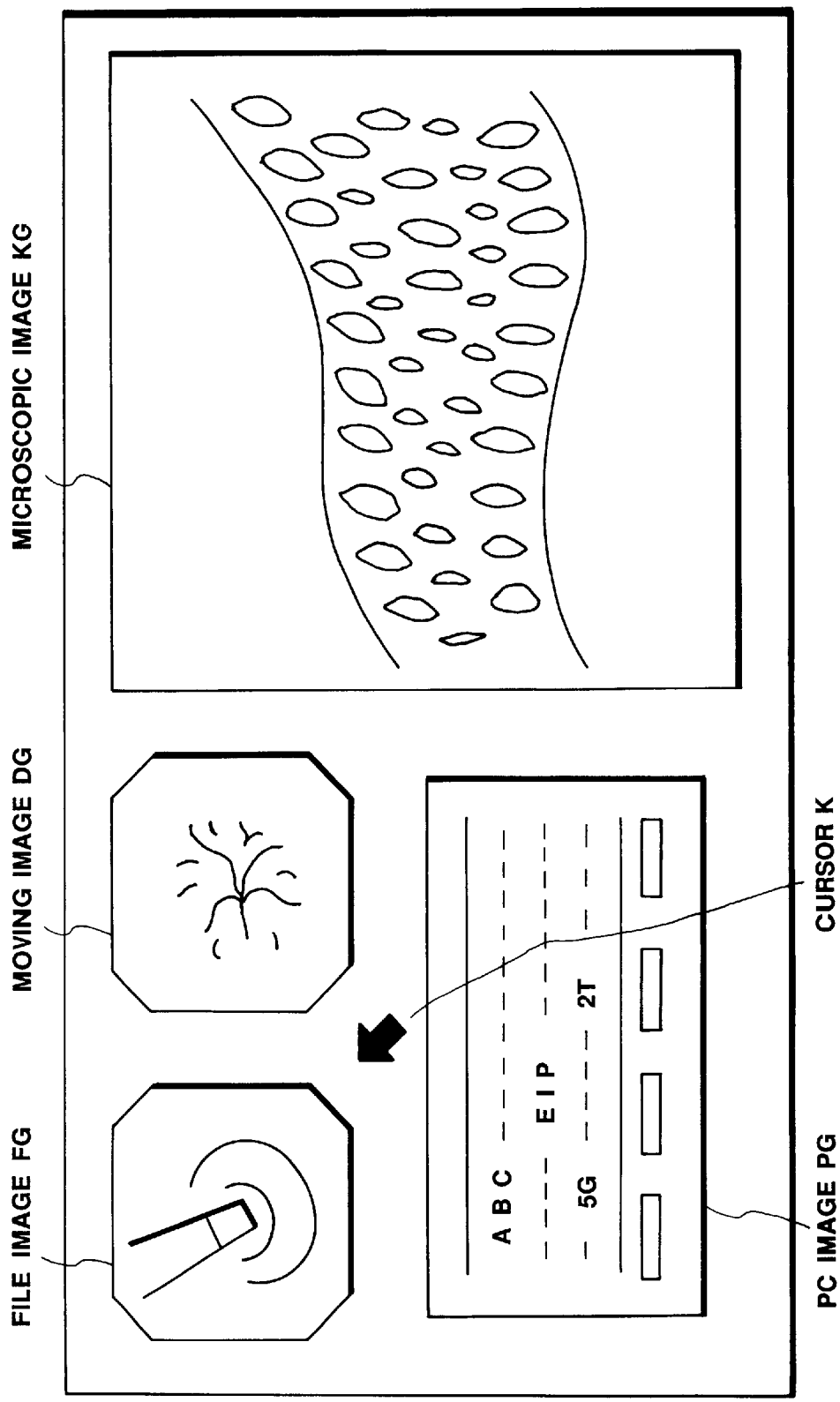

The various types of image data thus written into the corresponding frame memories are read at different timings in correspondence with a plurality of display regions (such as those shown in FIG. 7), and then sent, via an image bus and the D/A converter 21, to the hi-vision monitor 103, which displays in a manner such as that shown in FIG. 9.

Figure 8:
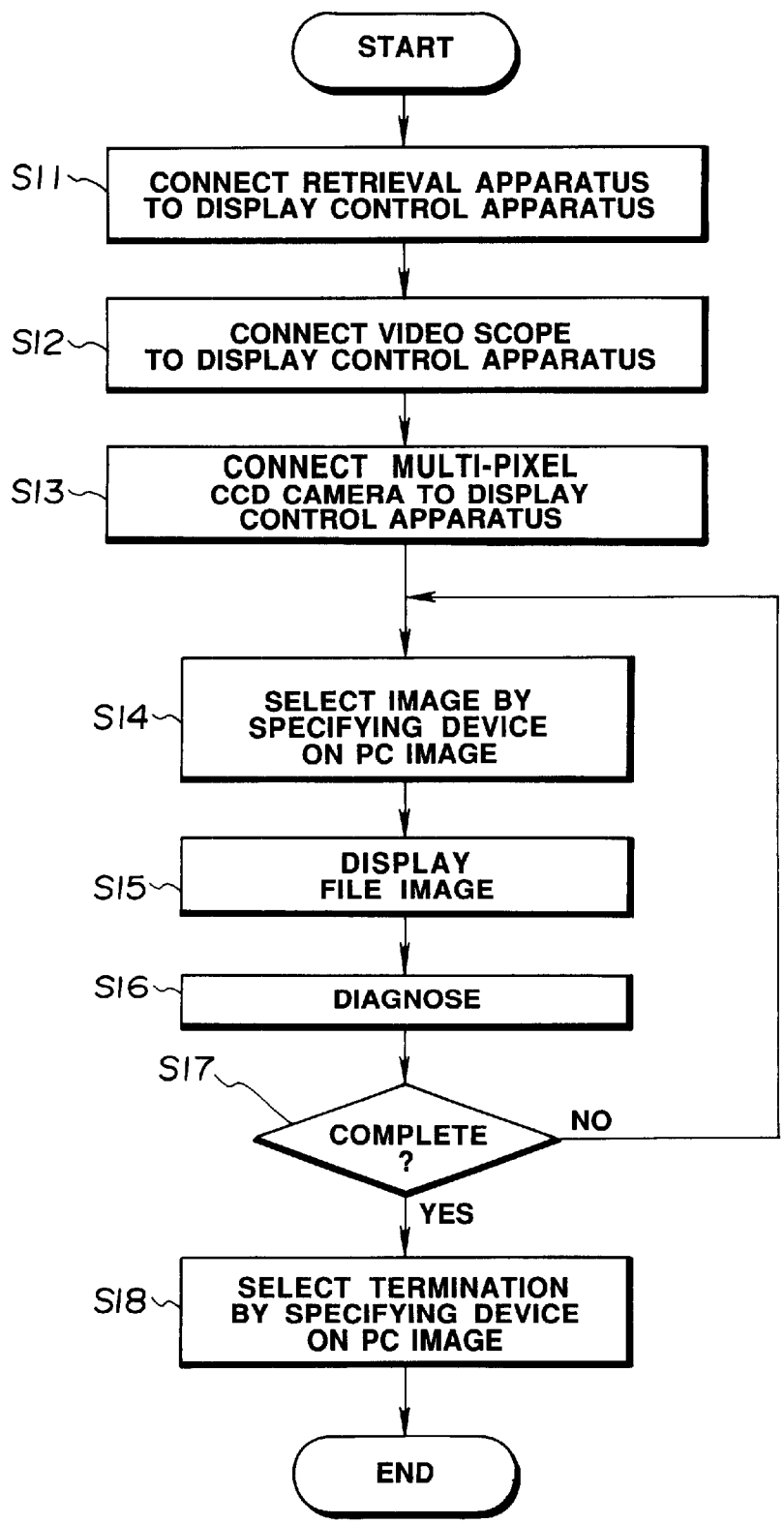

FIG. 8 shows the details of a typical operation performed in examination employing the endoscopic image display system 101. After the examination has started, the image the retrieval apparatus 104 is connected to the image display control apparatus 102 (Step S11) so that a PC image PG will always he displayed at a display position on the screen of the hi-vision monitor 103 which corresponds to the PC image region shown in FIG. 7. In Step S12, the video scope apparatus 107 is connected to the image display control apparatus 102 so that a video scope image (moving image DG) will always be displayed at another display position on the screen which corresponds to the moving image region shown in FIG. 7. These Steps S11 and S12 are similar to the first two steps in the first embodiment. Then, in Step S13, the multi-pixel CCD camera apparatus 109 is connected to the image display control apparatus 102 so that an observation image of the microscope 109 (microscopic image KG), obtained by the multi-pixel CCD camera apparatus 109, will always be displayed at still another display position on the screen of the hi-vision monitor 103 which corresponds to the multi-pixel CCD image region shown in FIG. 7.

Subsequently, the retrieval function of the PC 4 is started. Specifically, when, in Step S14, one of the images already recorded in the external recording apparatus 105 is selected by means of the specifying device 106 on the PC image, the selected image is, in Step S15, read from the external recording apparatus 105 and displayed as a file image FG on the screen of the hi-vision monitor 103.

Accordingly, the operator is able to simultaneously observe all of the video scope image, the file image and the microscopic image of the lesion portion, to thereby make a comprehensive diagnosis, in Step S16.

Thereafter, if it is determined, in Step S17, that the examination is not yet to be completed, Step 314 is again executed. On the other hand, if it is determined, in Step S17, that the examination is to be completed, Step S18 is effected, in which termination is selected by means of the specifying device 106 on the PC image, thereby terminating the flow for this examination.

Thus, according to the second embodiment, similarly to the case of the first embodiment, it is possible to simultaneously display an image for a retrieval-effecting operation on the same monitor that displays an endoscopic image, and hence, possible to perform a retrieval operation and the recognition of a retrieved endoscopic image while a single screen is being watched. The system of the second embodiment thus enables all of (i) a moving image DG obtained by the video scope apparatus which visualizes the affected portion, (ii) a file image FG from an image file, and (iii) a microscopic image KG of the lesion portion observed by the microscope to be compared with each other without reducing the resolution, thereby providing an environment with which a diagnosis can be easily made.

The video scope apparatus may be substituted with an external-TV-camera scope apparatus having a TV camera attached to a fiberscope.

It is apparent that widely different embodiments of the present invention may be made on the basis of the present invention without departing from the spirit and scope thereof, The present invention in not limited to any specific embodiment thereof except as defined in the appended claims.

What is claimed is:

1. An endoscopic image display system capable of always and simultaneously displaying (1) endoscope moving images under current examination obtained by an endoscope, (2) a plurality of reduced still endoscope images from former examinations which were conducted before the current examination, (3) non-reduced still images selected from among said plurality of reduced still endoscope images, and (4) character information related to at least one of said endoscope moving images, said reduced still images, and said no-reduced still images, in a predetermined region on a single monitor, comprising:

a recording apparatus for recording image signals;

a first image memory, operably coupled to said recording apparatus, for storing only said endoscope moving images in the form of said recorded image signals;

a second image memory, operably coupled to said recording apparatus, for storing only said reduced and non-reduced still images in the form of said recorded image signals;

a third image memory, operably coupled to said recording apparatus, for storing only said character information as a retrieval-character image signal; and display control means, operably coupled to said first, second and third image memories, for switching outputs of said memories of each of said images between said first, second and third image memories in every corresponding display region sequentially and for outputting the plurality of image signals to said monitor in accordance with the switching operation.

2. An endoscopic image display system according to claim 1, wherein said monitor is a hi-vision monitor and said display control means further has high-resolution image control means for inputting said recorded image signals in the form of high-resolution image signals from a multi-pixel imaging means having a multi-pixel solid-state imaging device, and for outputting said high-resolution image signals to said hi-vision monitor.

3. An endoscopic image display system according to claim 2 wherein said high-resolution image control means inputs a signal indicative of an observation image obtained by a multi-pixel imaging means, and outputs said observation image signal to said hi-vision monitor.

4. An endoscopic image display system according to claim 2 wherein said high-resolution image control means inputs a high-resolution image signal from a multi-pixel imaging means adapted for a hi-vision system, and outputs said high resolution image signal to said hi-vision monitor.

5. An endoscope image display system according to claim 1, wherein said recorded image signals consist of high-resolution image signals from a multi-pixel imaging means having a multi-pixel solid-state imaging device.

* * * * *